(12) United States Patent
Biedermann et al.

(10) Patent No.: US 6,695,843 B2
(45) Date of Patent: Feb. 24, 2004

(54) FIXING ELEMENT

(75) Inventors: Lutz Biedermann, VS-Villingen (DE); Jürgen Harms, Karlsruhe (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 10/034,290

(22) Filed: Dec. 21, 2001

(65) Prior Publication Data

US 2002/0082602 A1 Jun. 27, 2002

(30) Foreign Application Priority Data

Dec. 22, 2000 (DE) .......................... 100 64 571

(51) Int. Cl.⁷ .......................... A61B 17/56; A61B 17/58
(52) U.S. Cl. ........................................... 606/61
(58) Field of Search ............................. 606/61, 65, 72, 606/73; 411/15, 427, 44

(56) References Cited

U.S. PATENT DOCUMENTS

| 5,360,431 A | | 11/1994 | Puno et al. ..................... 606/72 |
|---|---|---|---|
| 5,549,608 A | * | 8/1996 | Errico et al. ................... 606/61 |
| 5,607,426 A | * | 3/1997 | Ralph et al. ................... 606/61 |
| 5,630,817 A | | 5/1997 | Rokegem et al. ............. 606/61 |
| 5,882,350 A | * | 3/1999 | Ralph et al. ................... 606/61 |
| 5,961,517 A | * | 10/1999 | Biedermann et al. ......... 606/61 |
| 6,471,705 B1 | * | 10/2002 | Biedermann et al. ......... 606/61 |

FOREIGN PATENT DOCUMENTS

| WO | WO 98/32386 | | 7/1998 |
|---|---|---|---|
| WO | WO 01/08574 | A1 | 2/2001 |

* cited by examiner

*Primary Examiner*—David O. Reip
(74) *Attorney, Agent, or Firm*—George W. Neuner; Edwards & Angell LLP

(57) ABSTRACT

A bone screw, known per se, with a thread section (2) and a receiving part (5) for receiving a rod (29) to be connected to the bone screw is created. The connection and locking of the connection between bone screw and rod takes place via an outer nut (13). So that the connection has the necessary strength and durability, the outer nut (13) has on the inside a sleeve-shaped element (17), having a predetermined inner measurement, the outer diameter of which is almost identical to or slightly smaller than the diameter of the bore (8), and a pressure element (23) arranged therein. The pressure element (22) (sic) has at its end facing the floor of the bore (8) a first section (26), the outer measurement of which is larger than the predetermined inner measurement and which effects a widening of the element (17) when pressure is exerted on the rod (29) to be received.

10 Claims, 3 Drawing Sheets

FIXING ELEMENT

The invention relates to a fixing element according to the preamble of Patent claim 1.

A fixing element of this kind is known in the form of a bone screw from EP 0 614 649 A1. In this a securing nut to be screwed into the open bore is provided for perfect locking of the connection between rod and bone screw.

The object of the invention is to create a fixing element of the kind initially described which manages without an internal nut of this kind.

This object is achieved by the bone screw characterised in Patent claim 1.

Further developments of the invention are characterised in the subordinate claims.

The invention is now explained in greater detail in the description of an embodiment example using the figures.

Figure 1:
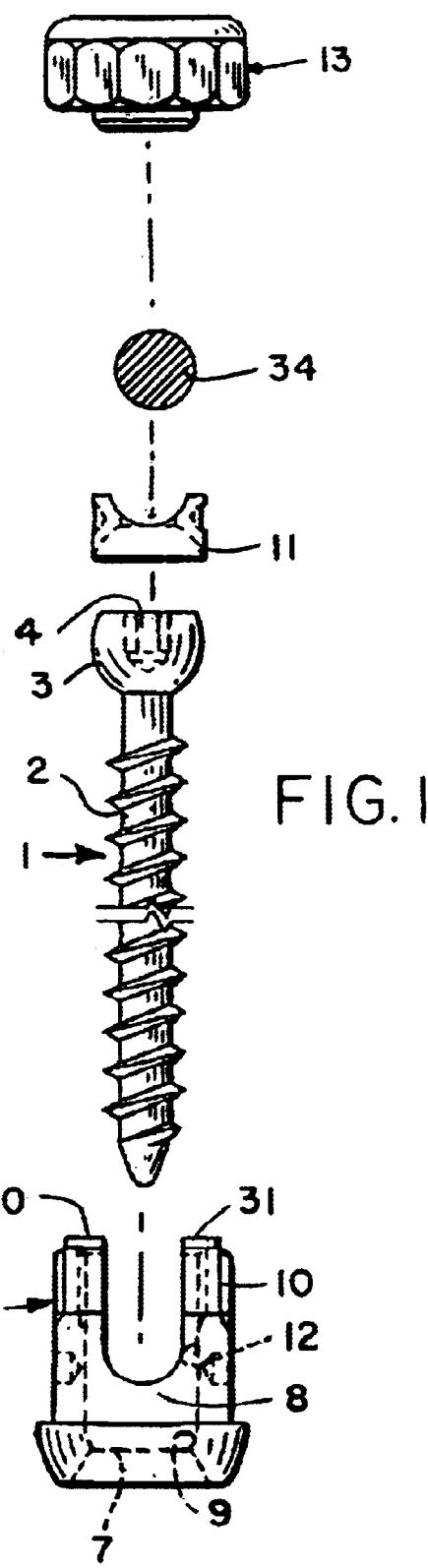
FIG. 1 shows an exploded-type side view of the bone screw.

The bone screw shown as an embodiment example comprises the actual screw element 1 with a thread section 2 and a head 3. Adjacent to the thread section the head is constructed in the shape of a segment of a ball. Coaxially to the thread axis and on the end opposite the thread section 2 the head has a recess 4 for bringing into engagement with an Inbus spanner.

The bone screw further comprises a cylindrically constructed receiving part 5. This has at one end an axially symmetrically aligned first bore 7, the diameter of which is larger than that of the thread section 2 and smaller than that of the head 3. The receiving part 5 further has a coaxial second bore 8, which is open at the end opposite the first bore 7 and the diameter of which is large enough for the screw element 1 to be guided through the open end with its thread section 2 through the first bore 7 and with the head 3 to the floor of the second bore. Between the first and the second bore a small coaxial section 9 is provided, which borders directly on the first bore and is constructed as spherical towards the open area, wherein the radius is substantially identical to the radius of the section of the head 3 shaped like the segment of a ball. The receiving part 5 further has a U-shaped recess 6, arranged symmetrically to the centre of the part, the floor of which is directed towards the first bore 7 and the two side legs 30, 31 of which extend towards the open end facing away from the first bore 7. An outer thread 10 is provided at the open end of the legs of the U-shaped recess.

On the side located at the open end of the head 3 is a pressure disc 11, which is constructed in such a way that on its side facing the head 3 it has a spherical depression, the radius of which is substantially identical to the radius of the section of the head shaped like the segment of a ball. The outer diameter of the pressure disc 11 is chosen in such a way that it can perform a sliding movement into the cylindrical section 12 of the second bore 8, in other words can be displaced in the cylindrical section towards the head. The pressure disc has a coaxial bore which enables access to the recess 4.

Figure 3:
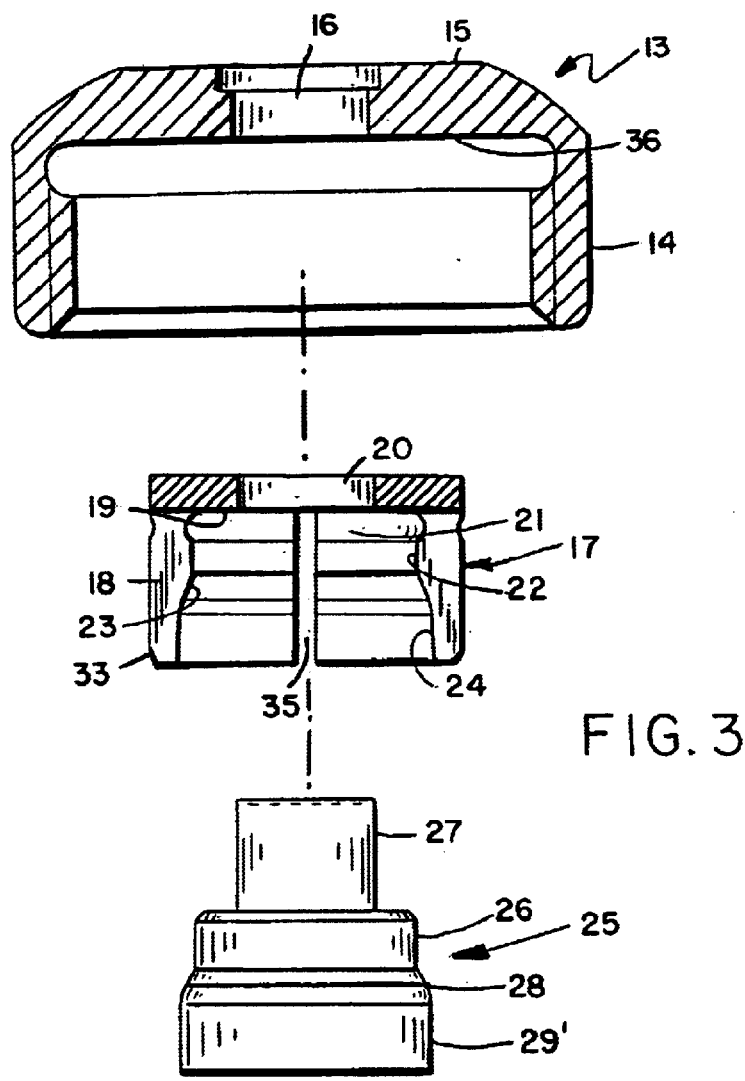
FIG. 3 shows an exploded representation of the outer nut in enlarged scale, partially bisected.
Figure 4:
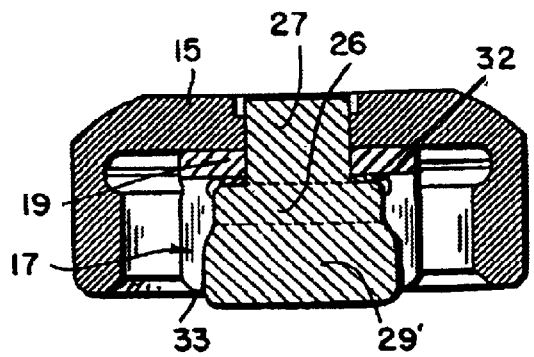
FIG. 4 shows the outer nut in assembled state before action on a rod.
Figure 5:
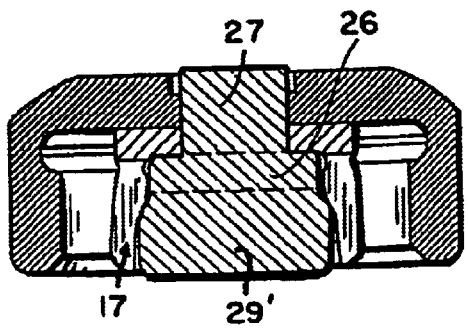
FIG. 5 shows the same representation after action on the rod.

The bone screw further comprises an outer nut 13, which is explained further in detail in particular by means of FIGS. 3 to 5. The outer nut is constructed as a capped nut and has a cylindrical side edge with an inner thread section 14, which forms the actual nut, and a cover part 15, adjacent to one edge of the thread section 14. The cover part is constructed as in a normal capped nut, but has additionally a concentric bore 16 with a first diameter. A sleeve 17 is further provided, which has a casing 18 and on its side facing the cover part 15 a floor 19. Provided in the floor 19 is a concentric bore 20 with a second diameter. The second diameter is identical to the first diameter of the bore 16 or a little larger.

As can best be seen from FIG. 3 the casing 18 has an inner space adjacent to the floor 19, which comprises a cylindrical wall section 22, which ends at a predetermined distance from the floor. In the embodiment example shown an undercut is located between the cylindrical wall section 22 and the floor, the diameter of which is at least equal to the diameter of the cylindrical wall section 22. Basically the cylindrical wall section can also extend to the floor 19 itself. As can be seen from FIG. 3, on the inside of the casing a wall section 23, running convergently outwards, adjoins the edge of the cylindrical wall section 22 facing away from the floor 19 and is slanted outwards in such a way that it has the shape of a section of a cone, wherein the angle of inclination of the slant with respect to the cylindrical inner wall is approximately 30° to 60° and preferably approximately 40°. The outer diameter of the outside cylindrical sleeve 17 is almost identical to the diameter of the second bore 8 and smaller than the latter by a sufficient amount for it just to be able to be inserted into the second bore 8 without friction.

As can further best be seen from FIG. 3, adjoining the truncated cone-shaped wall section 23, which becomes larger towards the outside, is a further wall section 24, which still increases outwards in diameter, in other words is again constructed as a conical section, but its inclination is only a few degrees. Alternatively this wall section 24 can also be constructed as cylindrical.

The outer nut further comprises a pressure element 25. This has a central first cylindrical section 26, the outer diameter of which is substantially identical to the inner diameter of the cylindrical wall section 22. It is dimensioned in such a way that the pressure element is held in the cylindrical wall section 22 by frictional force by inserting this section into the inside of the casing. On the side facing the floor 19 of the sleeve 17 a second cylindrical section 27 is provided, coaxially to the first cylindrical section. The diameter of this projection substantially corresponds to the diameter of the bore 16 and is dimensioned in such a way that this cylindrical section in the bore 16 is held in it by the frictional force. On the side of the first cylindrical section 26 facing away from the floor 19 a section 28, extending convexly, is provided which is constructed approximately in the shape of a conical section and faces the section 26 with its small diameter. The small diameter of this almost truncated cone-shaped section 28 is almost identical to the small inner diameter of the wall section 23, and the large diameter of the conical section 28 is almost identical to the large inner diameter of the wall section 23. The angle of section 28 is substantially equal to the angle of the wall section 23. A third cylindrical section 29 (sic)* adjoins section 28.

As can best be seen from FIG. 4, the pressure element 25 is pushed into the inside of the sleeve 17 until the convergent section 28 is resting on the inside of the sleeve. The dimensions of the pressure element in the axial direction are therein determined as follows: the axial length of the first cylindrical section 26 including a slanting edge, indicated in FIG. 4, is determined in such a way that when section 28 is adjacent to the inside of the sleeve between the floor 19 and the surface of the first cylindrical section 26 facing it there remains a slot-shaped distance 32 of preferably less than a millimeter. The length of the second cylindrical section 27 is identical to the length of the recess composed of bore 16 and bore 20. The axial length of the third section 29 (sic) is dimensioned in such a way that it projects, in the manner shown in FIG. 4 in the here described starting position, above the lower edge 33 of the sleeve 17 by a measurement which is greater than or at least equal to the measurement of the slot-shaped distance 32.

Figure 2:
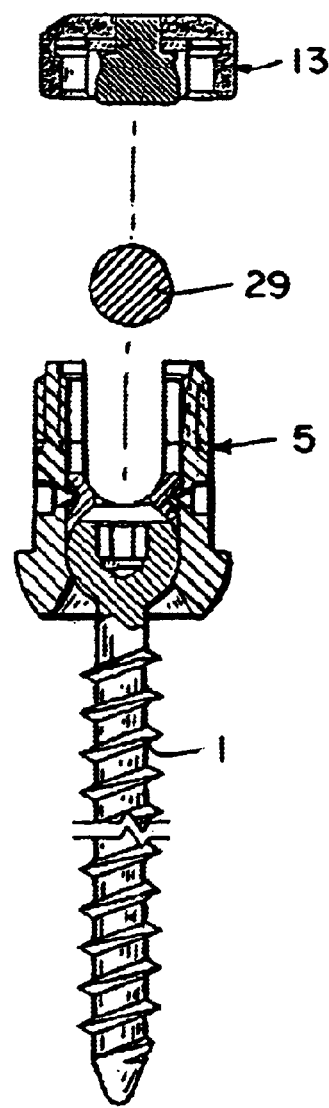
FIG. 2 shows a sectional representation through the bone screw.

In operation first the screw element 1, the receiving part 5 and the pressure disc are assembled in the way known per se, as can best be seen from FIG. 2. Then a rod 34 to be connected to the bone screw is inserted. The outer nut 13 is pre-mounted in the state which can be seen in FIG. 4, in other words the pressure element 25 is inserted into the sleeve 17 and together with this connected to the cover part 15. The thus pre-mounted nut is now screwed on to the outer thread of the receiving part 5. The rod 34 is therein located on the one hand on top of the pressure disc 11. On the other hand it is impacted with the pressure by the pressure element 22, which comes into contact with the rod during screwing on, so the outer nut 13 has almost reached the final position. When the outer nut 13 is further tightened into the desired final position the pressure element 25 is pushed to the floor, in the way shown in FIG. 5, which has the simultaneous result that the section 28 acts on the inner wall of the sleeve 17 in such a way that this is pressed slightly outwards, in the way shown in FIG. 5. This achieves that the casing 18 with its outer face in turn applies a force on to the exposed legs 30, 31 in the area of the outer thread 10 of the casing 18 comprising the inner thread.

As FIG. 3 shows best, the casing 18 has a multiplicity of slits 35, extending over the entire length of the casing, which are spaced apart in the circumferential direction and which make easier the above described process of widening the casing 18 when the pressure element 25 is pressed in.

By provision of the wall section 24 adjacent to the convex wall section 23, spreading out in the wall section 24 is achieved, which results in the outer diameter, without counter pressure from outside on to the sleeve in the area of the lower edge 33, being larger than the outer diameter of the sleeve in the area of the convex wall section 23. This enables a greater tolerance for the relative dimensioning of the outer diameter of the sleeve 17 relative to the inner diameter of the second bore 8, as even if the inner diameter of the second bore 8 is slightly larger than the outer diameter of the sleeve 17 a pressure is still exerted on the legs 30, 31, which is sufficient for locking. By means of this lengthening of the sleeve and dividing it up by the slits 35 into individual wall sections, these act as a kind of flectional beam, so locking also takes place more elastically.

In the above-described embodiment example this is a so-called polyaxial screw, in which the screw element 1 and the receiving part 5 can be moved at an angle relative to one another. In a modified embodiment the screw element 1 and a receiving part receiving the rod 34 are constructed in one piece with one another, possibly such that, in the way shown in FIG. 2, the receiving part 5, the head 3 and the pressure disc 11 are constructed as one piece. The outer nut 13 has in this case the identical above-described shape. In operational mode stopping of the outer nut 13 takes place by action of the force from the rod 34 on to the pressure element 25 in the above-described way, so the same locking is achieved.

Figure 6:
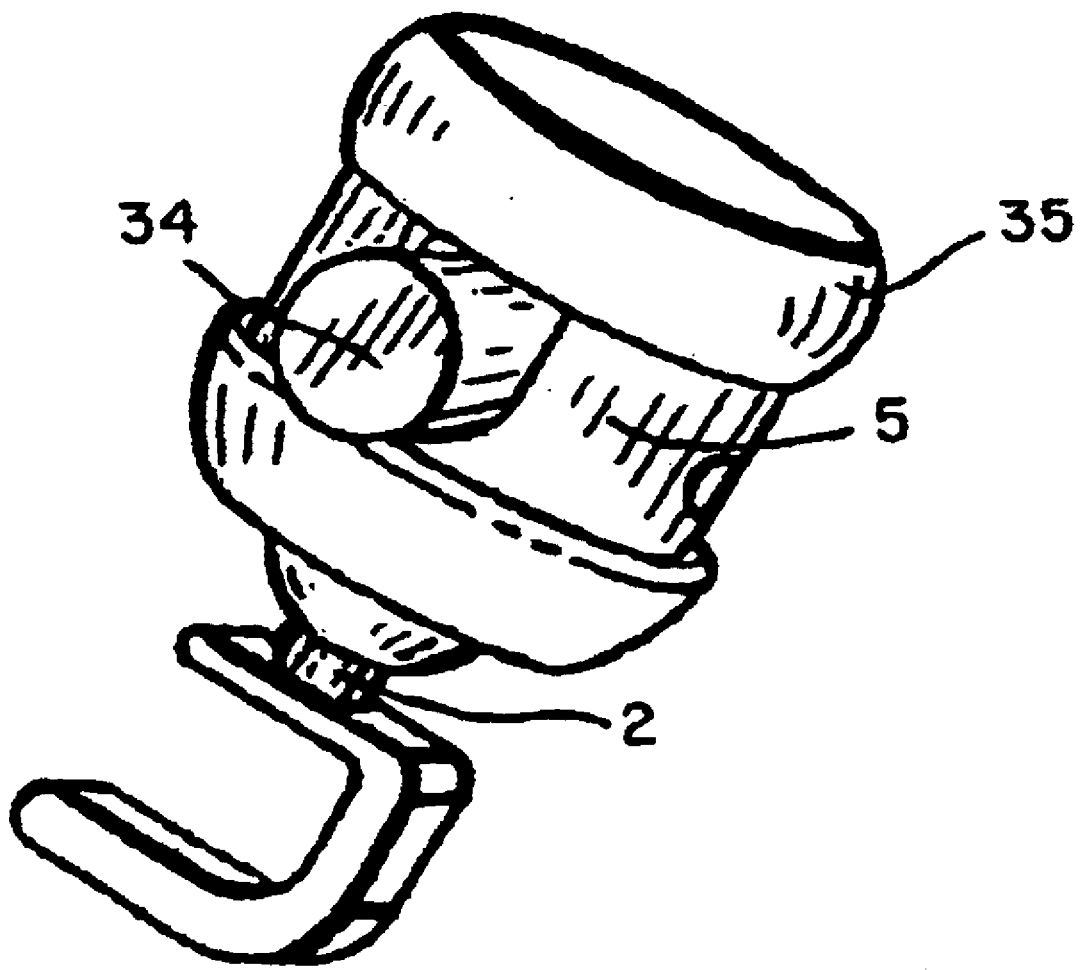
FIG. 6 shows a modified embodiment.

The embodiment shown in FIG. 6 is different from the embodiments described using FIGS. 1 to 5 only in that instead of the screw element 1 with the thread section 2 a shank 36 with a hook 37 is provided. All other elements coincide fully with the previously described elements. The hook is of a kind which is hooked in particular on the rear bone projections of the spinal column, e.g. on the lamina arches, in transverse extensions or in inter-vertebral spaces. The shape and dimensions are known from the general prior art.

In the above-described embodiment examples the sleeve 17 has a floor 19. In a modified embodiment the sleeve 17 has no floor. The sleeve is then directly adjacent to the inner side 36 of the cover part 15 and the gap 32 is correspondingly formed between the surface of the first cylindrical section 26 facing the inner side and the inner side 36. The length of the second cylindrical section 27 is then identical to the length of the bore 16.

What is claimed is:

1. A fixing element comprising:

a shank having a head side;

an outer nut;

a cylindrical receiving part on the head side for receiving a rod to be connected to the fixing element, wherein the receiving part has an open bore and a substantially U-shaped cross-section with two exposed legs having an outer thread;

wherein the outer nut comprises an edge, an inner thread and a cover part, wherein the outer nut can be screwed on to said outer thread, said outer nut further comprising an interior containing a sleeve-shaped element;

the sleeve-shaped element having a predetermined inner measurement and comprising a casing, a first surface facing the cover part, a second surface facing away from the cover part, an inner first wall section with a first diameter, an inner second wall section following in the direction of the second surface and running convexly in the direction of the second surface, and a third wall section adjacent to the inner second wall section;

wherein the outer diameter of the casing is almost identical to or slightly smaller than the diameter of the bore; and a pressure element structured and arranged to be positioned in the casing, wherein the pressure element has a first section, the first section having an outer diameter that is larger than the first diameter and that effects a widening of the casing when pressure is exerted on the receiving rod.

2. The fixing element according to claim 1, wherein the casing comprises a slit toward the second surface.

3. The fixing element according to claim 1, wherein the pressure element further comprises a second section adjacent to the first section on an end away from the cover part.

4. The fixing element according to claim 3, wherein the second section is cylindrical.

5. The fixing element according to claim 1, wherein the shank comprises a thread section on an end opposite the head side.

6. The fixing element according to claim 5, wherein the casing comprises a slit toward the second surface.

7. The fixing element according to claim 5, wherein the pressure element further comprises a second section adjacent to the first section on an end away from the cover part.

8. The fixing element according to claim 7, wherein the second section is cylindrical.

9. The fixing element according to claim 5, wherein the shank comprises a thread section on an end opposite the head side.

10. The fixing element according to claim 1, wherein the sleeve-shaped element has a cylindrical wall section of predetermined length on a side facing away from the cover part and the pressure element has a first cylindrical section that engages with the cylindrical wall section.

\* \* \* \* \*